United States Patent [19]

Korostoff et al.

[11] 4,153,060
[45] May 8, 1979

[54] METHOD AND APPARATUS FOR ELECTRICALLY ENHANCED BONE GROWTH AND TOOTH MOVEMENT

[75] Inventors: Edward Korostoff, Philadelphia, Pa.; Zeev Davidovitch, Cherry Hill, N.J.

[73] Assignee: University of Pennsylvania, Philadelphia, Pa.

[21] Appl. No.: 886,775

[22] Filed: Mar. 15, 1978

[51] Int. Cl.² ............................................. A61N 1/36
[52] U.S. Cl. ................................ 128/419 F; 32/14 R; 128/787
[58] Field of Search ............ 128/82.1, 419 F, 419 R, 128/409; 32/14 R, 14 E

[56] References Cited

U.S. PATENT DOCUMENTS

| 592,878 | 11/1897 | Morhard | 128/409 |
|---|---|---|---|
| 1,389,662 | 9/1921 | Irwin | 128/409 |
| 3,092,907 | 6/1963 | Traiger | 32/14 E |
| 3,842,841 | 10/1974 | Brighton et al. | 128/419 F |
| 3,918,459 | 11/1975 | Horn | 128/419 R |

*Primary Examiner*—William E. Kamm
*Attorney, Agent, or Firm*—Holman & Stern

[57] ABSTRACT

Disclosed is a method and apparatus for electrically stimulating bone growth and tooth movement in the mouths of mammals. A positive electrode is placed on the gum surface adjacent the bone structure which is to be resorbed. A negative electrode is placed on the gum surface adjacent the bone tissue which is to be accreted or built up. A current source is connected, such that a small current flows between the electrodes, which has the effect of stimulating bone growth in a specific direction. In a preferred embodiment, the electrodes are placed on the gum surface adjacent a tooth, the positive electrode on the side towards which the tooth should move, and the negative on the side from which the tooth will move. Application of a small current to the electrodes will enhance the repositioning of the tooth in conjuction with normal orthodontic practices.

16 Claims, 7 Drawing Figures

METHOD AND APPARATUS FOR ELECTRICALLY ENHANCED BONE GROWTH AND TOOTH MOVEMENT

BACKGROUND OF THE INVENTION

The present invention relates to orthodontic techniques in general, and the reduction in time required for specific tooth movement in particular.

Orthodontic tooth movement presently is accomplished by the application of mechanical forces to teeth. An apparatus is connected inside the mouth of a patient which applies, through the use of springs, rubber bands, or other means, a mechanical force in the direction of desired tooth movement. These forces cause the bone to resorb (be moved) in the direction of force and cause the bone to grow on the other side of the tooth.

This process of orthodontic force application enables teeth to move in the mouth within the boundaries of the neighboring tissues. The tooth movement is clarified by Wolff's Law which states, in effect, that bone under mechanical stress is remodeled to accomodate or reduce the stress. The unfortunate practical aspect to known techniques of orthodontic movement is that the mechanical apparatus, or "braces", must be worn by the patient for extended periods of time, often several years or more.

U.S. Pat. No. 3,842,841 teaches the application of a direct current to aid healing of bone fractures in the human body, but requires surgical implantation. A negative electrode (cathode) is surgically inserted into the site of a fracture, and a positive electrode (anode) is taped to the skin elsewhere. Although the precise biological process is not understood, the current flowing through the factured bone increases the healing rate of the damaged bone tissue.

However, to date, there have been no substantial improvements in enhancing tooth movement to reduce the total amount of time over which an orthodontic appliance must be used in order to accomplish a given amount of tooth movement or repositioning.

SUMMARY OF THE INVENTION

Therefore, in view of the foregoing, it is an object of the present invention to reposition teeth in a patient's mouth by applying an electrical potential to the patient's gums in the immediate vicinity.

It is a further object of the present invention to increase the rate of movement of teeth undergoing mechanical stress in accordance with known orthodontic practices.

It is a still further object of the present invention to provide an electronic circuit capable of being retained in conjunction with an existing orthodontic appliance for providing a constant current output to electrodes located adjacent to a tooth to be repositioned.

It is an additional object of the present invention to provide a method and apparatus for stimulating and controlling bone growth in a patient's mouth in order to correct alveolar bone defects, close cleft palates, or maintain the alveolar ridge in edentulous patients (those who have lost their teeth).

In accordance with the above, the other objects, a method and apparatus for the initiation and enhancement of tooth movement comprises the disposition of an anodic electrode in the direction of applied force and a cathodic electronic on the opposite side of the tooth to be moved. A current source is connected to the two electrodes which causes the tooth to be repositioned either solely or in combination with an existing orthodontic appliance.

The application of a small current, through appropriate surface electrodes in the mouth, also can be utilized to stimulate bone accretion in the vicinity of a cathodic electrode and bone resorption in the vicinity of an anodic electrode.

BRIEF DESCRIPTION OF THE DRAWINGS

A more complete appreciation of the invention and the attendant advantages thereof will be more clearly understood by reference to the following drawings wherein.

DETAILED DESCRIPTION OF A PREFERRED EMBODIMENT

Figure 1:
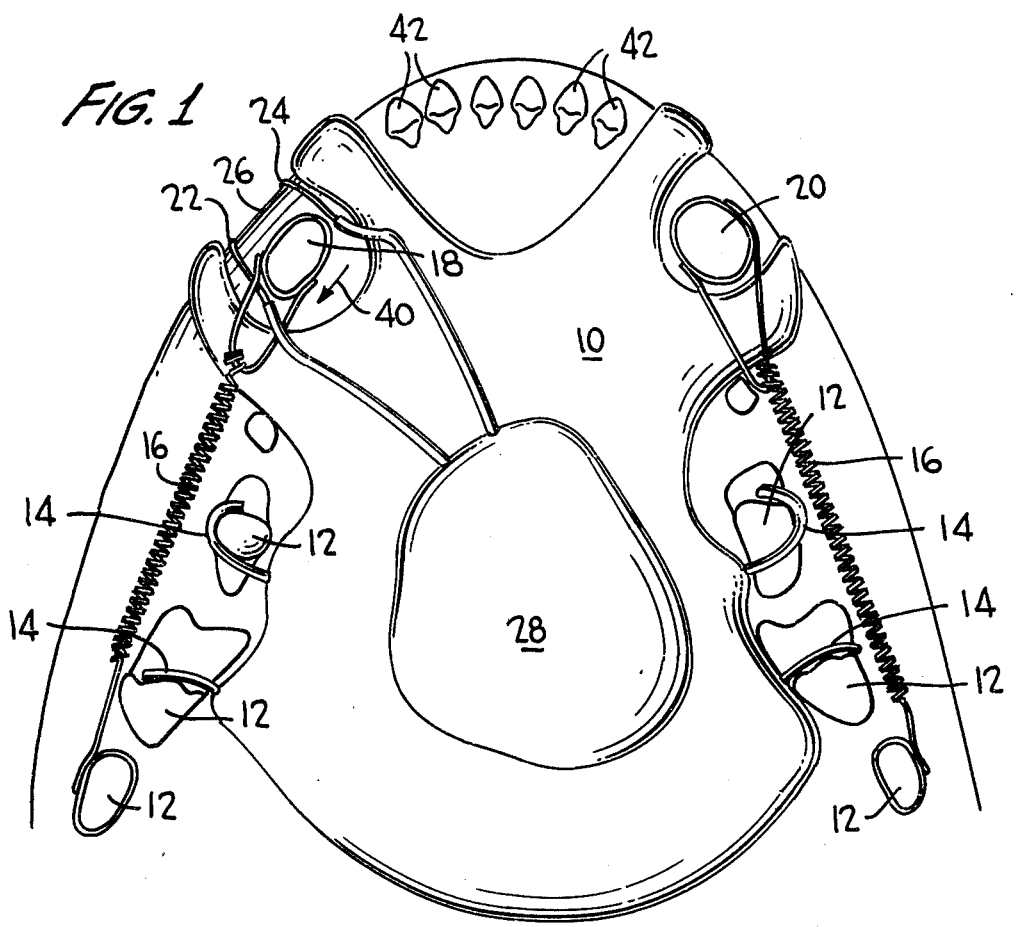
FIG. 1 is a bottom view of an orthodontic appliance showing the location of the apparatus in relation to the orthodontic springs.

Referring now to the drawings wherein like reference characters designate like parts throughout the several views, FIG. 1 is a bottom view of an orthodontic appliance along with the present invention fitted to a cat's mouth in accordance with known techniques. Although the present application was reduced to practice and demonstrated on a cat tooth, the anatomy and histology of the cat canine and its surrounding tissues is similar to one-rooted human teeth. Although the present description will be of the application of the present invention to the test animals, the invention is clearly of use in the human application, which would provide no unobvious difficulties. A base plate 10 is located in the roof of the patient's mouth and fixed to the premolar teeth 12 by conventional clamps 14. Orthodontic springs 16 are connected to the rearmost premolar teeth 12 and the teeth to be repositioned, in this instance, canine teeth 18 and 20.

An anode electrode 22 and a cathode electrode 24 are placed such that they are in contact with the gingival tissue 26. The anode 22 is placed adjacent the tooth in the direction of desired movement, in this instance, towards spring 16. The cathode 24 is placed on the opposite side of tooth 18. The anode 22 and cathode 24 are connected to positive and negative leads from power pack 28 contained in base plate 10.

Figure 4:
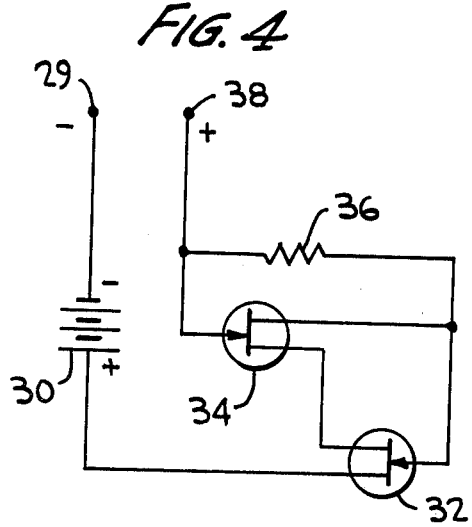
FIG. 4 is an electrical schematic of a preferred embodiment of a constant current circuit.

The details of the power pack's internal features can be seen by reference to FIG. 4. The negative terminal 29 is connected to the negative side of battery 30, with the positive side of the battery 30 connected to transistor 32. Transistor 32 is interconnected with transistor 34 and resistor 36 and, then, to the positive terminal 38. In this preferred embodiment, a constant current of approximately 20 microamperes is provided over a range of tissue impedances, such that the changing impedance between the anode and cathode does not substantially affect the amount of current flowing therebetween.

Figure 2:
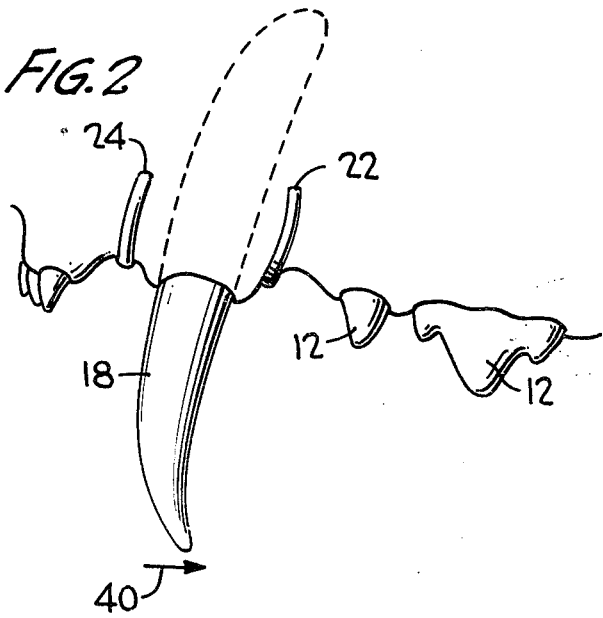
FIG. 2 is a side view showing the placement of the electrodes according to a preferred embodiment.
Figure 3:
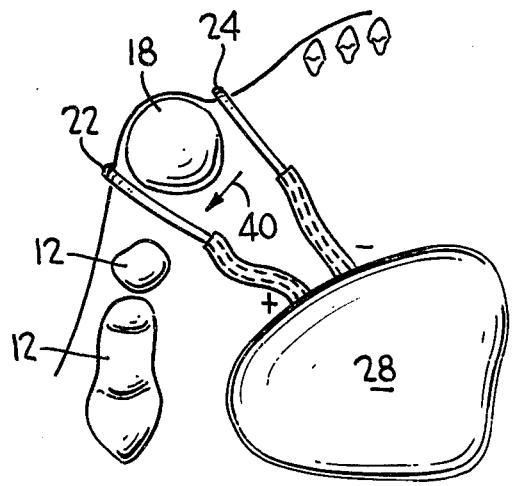
FIG. 3 is a bottom view showing a preferred embodiment of the anode and cathode electrodes.

FIGS. 2 and 3 are side and bottom views, respectively, of a preferred electrode placement, with the direction of desired movement shown by arrow 40. Although the mechanical force generating system comprising orthodontic springs 16, shown in FIG. 1, are not included in FIGS. 2 and 3, they could clearly be added to further enhance the movement of tooth 18 in direction 40. However, tooth movement can be accomplished solely by means of the electrical stimulation shown in FIGS. 2 and 3, and this remains one embodiment.

However, the preferred embodiment of the present invention is the use of the electrodes to increase the rate of movement of teeth undergoing orthodontic treatment.

In a test of the FIG. 1 apparatus, five female cats (Group A) had both canine teeth tipped in the direction of arrow 40 by coil springs generating 80 grams of force for a period of 14 days. Five additional female cats (Group B) had both canines tipped in the same direction. However, Group B cats also had a stainless steel cathode 24 and a gold anode 22 connected to the electrical circuit of FIG. 4, with the electrode placement shown in FIG. 1. Both electrodes were in contact with the gingival tissues at, and partially surrounding, the area of the alveolar bone crest. Dummy electrodes (not shown) were also placed in contact with the gingival tissues surrounding canine tooth 20, but were not connected to power pack 28.

In the Group A animals, the rate of canine tooth movement was similar on both sides. In Group B, however, the rate was unequal with the activated electrode side doving canine tooth 18 twice as much as electrically unactivated canine tooth 20. For instance, the distance between incisors 42 and unactivated canine tooth 20 increased by 0.29 mm after seven days, and an additional 0.17 mm after fourteen days. The distance between the incisors 42 and the electrically activated canine 18 after seven days had increased 0.58 mm, and after fourteen days an additional 0.61 mm. Because both canine teeth 18 and 20 had identical mechanical forces applied thereto (by springs 16), the increased rate of movement of canine tooth 18 is attributable to the application of electric current to the surrounding gum tissues.

Because the present invention essentially doubles the rate of movement, the length of time necessary to achieve a repositioning of a tooth would be cut in half. Although human tests have not yet been conducted, it is believed the results will be similar to those shown in the cat studies, because of the similarity of cat canine teeth and their surrounding tissues to single root human teeth. Thus, the applicability to the human orthodontic patient is believed obvious in view of the above teachings. The application to the human patient may require current levels different from the 21 microamps applied in the cat embodiment.

Similarly, different combinations of implanted and surface electrodes will be obvious to those of ordinary skill in the art in view of the applicants' teachings. Although, a constant current supply source was utilized in a preferred embodiment, constant voltage with a variable current source may be used with slightly different results. Additionally, an alternating current with a D.C. impressed thereon would also work. The only requirement being that one electrode be substantially anodic and the other substantially cathodic, i.e., the total current (AC and DC combined) is more in one direction than the other.

The current supply means utilized in the cat tests delivered a constant current of $21 \pm 4$ $\mu$ amps. It is believed that some variation may be necessary for individual patients, but that current ranges of between 5 and 100 microamps will be useful in obtaining similar results in humans. Additionally, where, as will be seen, extended electrodes are utilized, as in FIGS. 6 and 7, the total current applied to the extended electrode (or a series of button electrodes) must be increased in order to maintain a current density at the gum tissue, sufficient to cause bone accretion or resorption.

The present embodiments indicate the placement of electrodes on the soft gingival tissue adjacent, but not in contact with, the bone in order to produce the desired effect, although there is no indication that placement of the electrodes on the bone itself would have a deleterious effect. A preferred circuit for a constant current power supply is shown in FIG. 4, although many compact intra-oral power supplies will become apparent to those skilled in the art in view of the applicants' invention.

Figure 5:
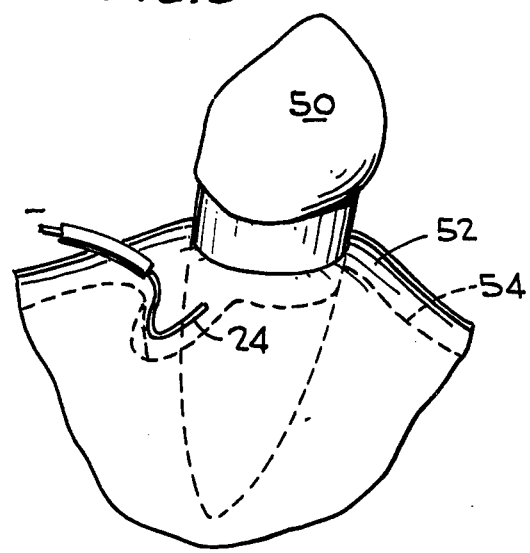
FIG. 5 is a perspective view showing the placement of the cathode electrode to correct aveolar bone defects.

The application of surface electrodes to stimulate controlled bone growth can also supply the solution for non-surgical correction of alveolar bone defects, and cleft palates. FIG. 5 depicts a tooth 50, gum 52, with the alveolar bone ridge 54. A defect in the alveolar bone ridge is indicated at 56. The placement of a cathodic surface electrode 24 on the gum in the region of the defect 56 could stimulate bone growth so as to eliminate the defect. The anodic surface electrode (not shown) would be located elsewhere in the patient's mouth.

Figure 6:
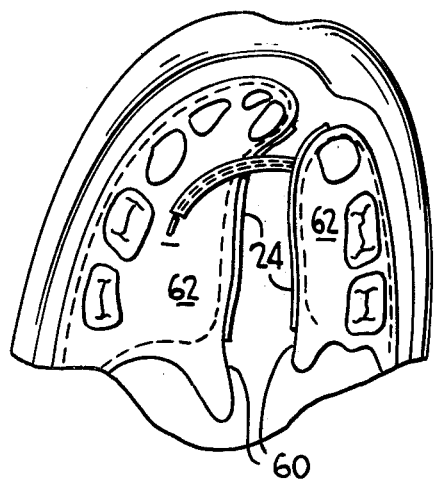
FIG. 6 is a bottom view of the placement of cathode electrodes for the correction of a cleft palate.

A similar application of the surface electrode could be utilized in conjunction with a cleft palate, as shown in FIG. 6. The region of the cleft 60 would be gradually filled by bone due to the electrical stimulation of cathodic electrodes 24 placed on the surface of tissues covering the bony palate 62. As in FIG. 5, the anodic electrode would be located elsewhere in the patient's mouth. As in all depictions of the use of surface electrodes, only in the region where bone growth is to be stimulated, or the bone is to be resorbed, is the electrode in contact with the gum, or gingival tissues. Elsewhere, the wires connecting the surface electrodes to the power supply would be insulated so as to restrict bone accretion, or resorption, to the desired area. It has been proposed that over an extended period of time, the bone accretion to the bony palate in the vicinity of electrodes 24 would result in a buildup, and eventual closure, of the cleft region 60 in the victim of a cleft palate.

It has been found that the bone has piezoelectric properties: that is to say, when a force is applied to the tooth, the resulting force on the bone generates very small, but measurable, electrical currents. It is believed that the application of these minute currents stimulate, and maintain, the alveolar bone ridge, which serve as the base for anchoring of human teeth. However, edentulous patients suffer from a gradual resorption of the alveolar bone ridge in the mouth, which makes it more and more difficult to anchor false teeth in the patient's mouth. It is believed that the absence of real teeth in the edentulous patient causes the termination of the minor stimulation currents necessary for the maintenance of the alveolar bone ridge and, consequently, the ridge resorbs into the roof of the mouth.

Figure 7:
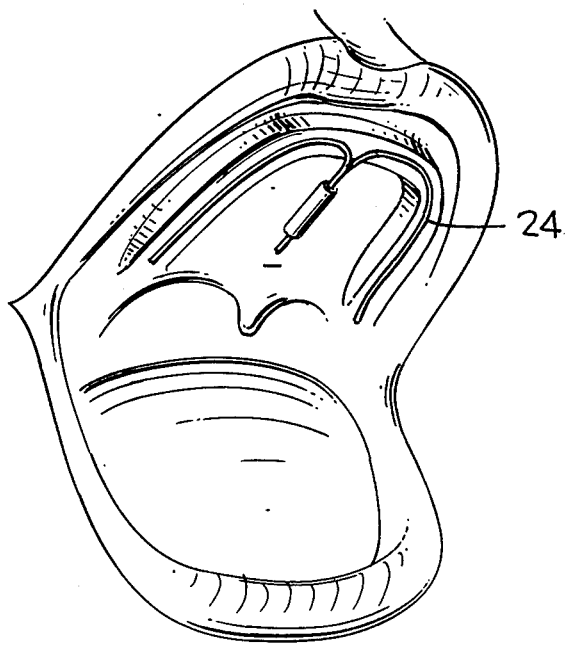
FIG. 7 is a perspective view showing the placement of the cathode electrode in an edentulous patient.

FIG. 7 depicts an arrangement of cathodic electrode 24, wherein it would be placed adjacent the alveolar bone ridge in a patient's mouth. The application of a suitable current supply with the anode (not shown) located elsewhere in the mouth may provide sufficient stimulation to the alveolar bone ridge, such that it is maintained, or even reformed, in the edentulous patient. Obviously, the power supply, and appropriate electrodes, could be located in the bridge work of false teeth, and would be applicable both to the upper and lower bond ridges.

Although the invention has been described relative to a specific embodiment thereof, it is not so limited and many modifications and variations thereof will be readily apparent to those skilled in the art in light of the above teachings. It is, therefore, to be understood that, within the scope of the appended claims, the invention may be practiced otherwise than as specifically described.

The embodiments of the invention in which an exclusive property or privilege is claimed are defined as follows:

1. A method of repositioning a tooth in the mouth of a patient, said method comprising the steps of:
    applying a substantially anodic surface electrode in the vicinity of said tooth to be repositioned, said anode electrode applied substantially at a point towards which said repositioning is desired and applying a substantially cathodic surface electrode in the vicinity of said tooth to be repositioned, said cathode electrode applied substantially opposite said anodic electrode; and
    causing a current to flow between said surface electrodes to cause repositioning of the tooth.

2. The method of claim 1, including the additional step of applying a force to said tooth in the desired direction of tooth movement.

3. The method of claim 1, wherein said electrodes are applied to the gingival tissues in the vicinity of, but not in contact with, the tooth to be repositioned.

4. An apparatus for the repositioning of a tooth in the mouth of a patient, said apparatus comprising:
    anodic electrode means, comprising a surface electrode, for applying a potential to the vicinity of said tooth to be repositioned and located substantially in the direction of desired repositioning;
    cathodic electrode means, comprising a surface electrode, for applying a potential to the vicinity of said tooth to be repositioned and substantially opposite said anode electrode means; and
    current means, connected to both said surface electrode means, for causing a current to flow therebetween, said current to cause repositioning of the tooth.

5. The apparatus of claim 4, wherein said surface electrodes are applied to the gingival tissues surrounding said tooth.

6. The apparatus of claim 5, wherein said apparatus includes means for applying a force to said tooth in said direction of desired movement.

7. The apparatus of claim 6, wherein said current means is a source of constant current flow during operation of the appartus.

8. The appartus of claim 7, wherein said cathodic electrode means comprises a stainless steel electrode and said anodic electrode means comprises a gold electrode.

9. In an orthodontic apparatus for causing tooth movement comprising means for applying stress to a tooth for the purpose of causing said tooth to change position, an improvement increasing the rate of movement of said tooth, said improved apparatus comprising:
    an anodic electrode placed on gingival tissues surrounding said tooth, said anodic electrode located adjacent said tooth and substantially in a direction of desired position change;
    a cathodic electrode placed on said gingival tissues adjacent said tooth and substantially in opposition to said anodic electrode; and
    current means, located in said orthodontic apparatus and electrically connected to said electrodes, for causing a current to flow between said anodic and cathodic electrodes, said current to cause an increase in the rate of movement of said tooth.

10. A method of correcting an alveolar bone defect in the mouth of a patient, said method comprising the steps of:
    applying a substantially cathodic surface electrode in the vicinity of said alveolar bone defect, and applying a substantially anodic surface electrode elsewhere in the mouth of said patient; and
    providing a current flow between said surface electrodes to cause accretion of the alveolar bone in the vicinity of the alveolar bone defect.

11. An apparatus for the correction of an alveolar bone defect in the mouth of a patient, said apparatus comprising:
    cathodic electrode means, comprising a surface electrode for applying a potential to the vicinity of said alveolar bone defect;
    anodic electrode means, comprising a surface electrode, for applying a potential elsewhere in the mouth of said patient; and
    current means, connected between said electrode means, for causing a current to flow therebetween, said current to cause bone accretion in the vicinity of said alveolar bone defect.

12. A method of non-surgically correcting the palatal bone structure in the mouth of a victim of cleft palate, said method comprising the steps of:
    applying a substantially cathodic surface electrode along opposing sides of said cleft palate with a substantially anodic surface electrode applied elsewhere in the mouth of said patient; and
    causing a current to flow between said surface electrodes to cause accretion on said bony palate in the region of said cathodic surface electrode closing said cleft palate.

13. An apparatus for the non-surgical correction of a cleft palate in the bony palate of the mouth of a patient, said apparatus comprising:
    cathodic electrode means, comprising a surface electrode, for applying a potential along opposing sides of said cleft palate;
    anodic electrode means comprising a surface electrode, for applying a potential elsewhere in said mouth; and
    current means, connected to both said surface electrodes for causing a current to flow therebetween, said current to cause accretion of bone to said bony palate closing said cleft palate.

14. A method of correcting and maintaining the alveolar bone ridge in the mouth of edentulous patients, said method comprising the steps of:

applying a substantially cathodic surface electrode in the vicinity of said alveolar bone ridge and applying a substantially anodic surface electrode elsewhere in the mouth of said patient; and causing a current to flow between said surface electrodes to cause stimulation and growth of the alveolar bone ridge.

15. An apparatus for the recreation and maintenance of the alveolar bone ridge in the mouth of an edentulous patient, said apparatus comprising:

cathodic electrode means, comprising a surface electrode, for applying a potential to the vicinity of said alveolar bone ridge in the mouth of said patient;

anodic elecrode means, comprising a surface electrode, for applying a potential elsewhere in the mouth of said patient; and current means, connected to both of said surface electrodes, for causing a current to flow therebetween, said current to cause stimulation and growth of said alveolar bone ridge.

16. An orthodontic kit for creating an orthodontic appliance to be fitted in a patient's mouth to cause movement of the patient's tooth in a desired direction, said kit comprising:

anodic electrode means for creating a positive surface electrode for placement on the gingival tissues surrounding said tooth, said electrode located substantially in a direction of desired tooth movement;

cathodic electrode means for creating a negative surface electrode for placement on said gingival tissues adjacent said tooth, said electrode located substantially in a direction away from which tooth movement is desired;

current means, compatible with placement in said orthodontic appliance and electrically connectable with said electrodes, for causing a current to flow between said anodic and cathodic electrode means, said current to cause an increase in the rate of movement of said tooth;

force application means for applying an orthodontic correctional force to said tooth in the direction of desired position change;

appliance means which can be molded to fit the mouth of said patient, for containing said current means and for maintaining said electrode means in position on said gingival tissues; and anchoring means for providing anchors to hold said appliance means in position in the mouth of said patient.

* * * * *

Disclaimer and Dedication 4,153,060.—*Edward Korostoff,* Philadelphia, Pa., and *Zeev Davidovitch,* Cherry Hill, N.J. METHOD AND APPARATUS FOR ELECTRICALLY ENHANCED BONE GROWTH AND TOOTH MOVEMENT. Patent dated May 8, 1979. Disclaimer and Dedication filed Jan. 20, 1982, by the assignee, *University of Pennsylvania.*

The term of this patent subsequent to July 20, 1993, has been disclaimed.
[*Official Gazette March 23, 1982.*]